United States Patent
Sowers et al.

(10) Patent No.: US 7,462,480 B2
(45) Date of Patent: Dec. 9, 2008

(54) STIMULATION OF MICROBIAL DECHLORINATION OF POLYCHORINATED BIPHENYLS WITH HALOGENATED ETHENES

(75) Inventors: Kevin R. Sowers, Baltimore, MD (US); Harold May, Mt. Pleasant, SC (US)

(73) Assignees: University of Maryland Biotechnology Institute, Baltimore, MD (US); Medical University of South Carolina, Charleston, SC (US)

( * ) Notice: Subject to any disclaimer, the term of this patent is extended or adjusted under 35 U.S.C. 154(b) by 300 days.

(21) Appl. No.: 10/502,920

(22) PCT Filed: Feb. 3, 2003

(86) PCT No.: PCT/US03/03202

§ 371 (c)(1),
(2), (4) Date: Jun. 17, 2005

(87) PCT Pub. No.: WO03/065011

PCT Pub. Date: Aug. 7, 2003

(65) Prior Publication Data

US 2006/0057705 A1    Mar. 16, 2006

Related U.S. Application Data

(60) Provisional application No. 60/353,134, filed on Feb. 1, 2002.

(51) Int. Cl.
*B09B 3/00*    (2006.01)
*B02F 3/34*    (2006.01)
*B09C 1/00*    (2006.01)

(52) U.S. Cl. ............... 435/262.5; 210/610; 210/611

(58) Field of Classification Search ............... None
See application file for complete search history.

(56) References Cited

U.S. PATENT DOCUMENTS

| | | |
|---|---|---|
| 4,876,201 A | 10/1989 | Bedard et al. |
| 4,950,309 A | 8/1990 | Schulz |
| 5,227,069 A | 7/1993 | Van Dort et al. |
| 5,242,601 A | 9/1993 | Manchak, Jr. et al. |
| 5,484,729 A | 1/1996 | DeWeerd et al. |
| 5,540,838 A | 7/1996 | Smullen et al. |
| 5,578,210 A * | 11/1996 | Klecka ................. 210/610 |
| 5,618,727 A | 4/1997 | Lajoie et al. |
| 5,635,393 A | 6/1997 | Bhatnagar et al. |
| 5,750,065 A | 5/1998 | Kilbane, II |
| 5,834,222 A | 11/1998 | Friedman et al. |
| 5,858,692 A | 1/1999 | Shibata et al. |
| 5,897,996 A | 4/1999 | Kimbara et al. |
| 5,922,204 A * | 7/1999 | Hunter et al. ............ 210/603 |
| 5,932,472 A | 8/1999 | Abdullah |
| 5,968,360 A | 10/1999 | Crowley et al. |
| 6,156,203 A * | 12/2000 | Anthony ................. 210/611 |
| 6,245,235 B1 * | 6/2001 | Perriello ................. 210/611 |
| 6,265,205 B1 * | 7/2001 | Hitchens et al. ........... 435/262 |
| 6,403,364 B1 * | 6/2002 | Hince .................. 435/262.5 |
| 6,488,850 B2 * | 12/2002 | Perriello ................. 210/605 |
| 6,946,248 B2 * | 9/2005 | Sowers et al. .............. 435/6 |

OTHER PUBLICATIONS

Adrian, et al., "Bacterial dehalorespiration with chlorinated benzenes," Nature, 408:508-583, 2000.
Maymo-Gatell et al., "Isolation of Bacterium the Reductively Dechlorinates Tetrachloroethene to Ethene," Science, 276:1568-1571, 1997.
Wu, et al., "Temperature Determines the Pattern of Anaerobic Microbial Dechlorination of Aroclor 1260 Primed by 2,3,4,6-Tertrachlorobiphenyl in Woods Pond Sediment," Appl. Eniron. Microbiol., 63:4818-4825, 1997.
Wu, et al., "2,6-Dibromobiphenyl Primes Extensive Dechlorination of Aroclor 1260 in Contaminated Sediment at 8-30 by Stimulation Growth of PCB-Dehaloginating Microorganisms," Environ. Sci. Technol., 33:595-602, 1999.
Seeger, et al., "Dehalogenation, Denitration, Dehydroxylation, and Angular Attack on Substituted Biphenyls and Related Compounds by a Biphenyl Dioxygenase," J. Bacteriol., 183(12):3548-3555 2001.
Megharaj, et al., "Recalcitrance of 1,1-dichloro-2,2bis(p-chlorophenyl)ethylene to degradation by pure cultures of 1,1diphenethylene-degrading anerobic bacteria," Appl. Microbiol. Biotechnol., 49(3):337-342, 1998.

* cited by examiner

*Primary Examiner*—Herbert J. Lilling
(74) *Attorney, Agent, or Firm*—Kelly K. Reynolds; Steven J. Hultquist; Intellectual Property/Technology Law (57) ABSTRACT

Disclosed is a method for the anaerobic microbial dechlorination of polychlorinated biphenyls (PCBs). Polyhalogenated ethenes are used to stimulate the growth and dechlorinating activity of PCB dechlorinating bacteria in a contaminated soil or sediment. This method may be further coupled with aerobic microbial degradation of PCBs for the complete destruction of PCBs in soils and sediments. Polyhalogenated ethenes are also used in growth media for the culturing of PCB dechlorinating bacteria.

32 Claims, 9 Drawing Sheets

SEQ ID NO 1 (RFLP17)

GAGTTTGATCCTGGCTCAGGATGAACGCTAGCGGGCGTGCTTATGCATGCAAGTCGAACG

GTTTTGAGTCTTGGACTTAAAATAGTGGCAAACGGGTGAGTAACACGTAGGTAACTT

ACCCCTAAGTTTGGGATAACTCCGGGAAACCGGGGCTAATACCGGATGTGGTGAGCGGGT

AATGCCTGTTCACTAAAGCCTTCGGGCGCTTGGGGAAAGGCCTGCGTCCGATTAGCTTGT

TGGTGGGGTAATGGCTCACCAAGGCTATGATCGGTAGCTGGCCTGAGAGGACGGTCAGCC

ACACTGGGACTGAGACACGGCCCAGACTCCTACGGGAGGCAGCAGCAAGGAATTTGGGC

AATGGGGGAAAGCCTGACCCAGCAACGCCGCGTGGGGATGAAGGCCCTCGGGTTGTAAA

CCCCTTTCCCAGGGAAGATGATGACGTACCTGGGAATAAGCCCCGGCTAACTACGT

GCCAGCAGCCGCGGTAATACGTAGGGGGCAAGCGTTATCCGGATTTACTGGGCGTAAAGA

GGACGTANGGGCGTTTCAAGTCGGATGTGAAATTCCCGGCTCAACCGGGATGAGTCAT

TCGATACTGTTGGCTAGAGGATAGCAGGGGAGACGGAATTCCCGGTGTAGTGGTGGAA

TACGTAGATACCGGGAGGAACACCAGAGGCGAAGGCGGTCTCCAAGGCTATTTCTGACGC

Figure 3B

TGAGGTCGGAAAGCGTGGGTAGCAAACAGACTTAGATACTCTGGTAGTCCACGCTGTAAA

CGATGGACACTAGGTATAGGGGAGCATCGACCCCTCTTGTGCCGAAGCTAACGCTTTAAGT

GTCCCGCCTGGGGACTACGGCCGCAAGGCTAAAACTCAAAGGAATTGACGGGGGCCCGCA

CAAGCAGCGGAGCGGTGTGGTTTAATTCGATGCAACGCGAAGAACCCTTACCAAGGCTTGAC

ATGTCGGAAGTAGTGAACCGAAAGGGGAACGACCCGTTAAATCGGAGCCGTCACAGGTG

CTGCATGGCTGTCGTCAGCTCGTGCCGTGAGGTGTATGGTTAAGTCCTGCAACGAGCGCA

ACCCTCGTCGCTAGTTGAATTCTCTAGCGAGACCGCCCTGCAAACGGGGAGGAAGGTGG

GGATGACGTCAAGTCAGCATGGCCCTTATGCCTTGGGCTACACACACGCTACAATGGGTG

GTACAGCAGGTAGCAATAGGTTAACCTGAGCTAATCCCTAAAACCATCCTCAGTTCGGAT

TGTAGGCTGAAACTCGCCTGCATGAAGCTGGAGTTGCTAGTAAACGGTATCAGCACGGC

GCGGTTGAATACGTTTCGGGCCTTGTACACACCGCCCGT

Figure 4

SEQ ID NO 2

ATGGCTGTGGTCGTGCCGTGAGGTGTTGGTAAGTCCTGCAACGAGC
GCAACCCTCATCGTTAGTGTTTCTAGCGAGACTGCCCTGCAAAACGGGGA
GGAAGGTGGGGATGACGTCAAGTCAGCATGGCCCTTATGCCTAGGCTACACA
CACGCTACAATGGGTGGTACAAATGGTTGCAATGGAGCAATCCGAGCCAATC
CGTAAAGCCACTCTCAGTTCGGATTACAGGCTGAAACTCGCCTGTATGAAGTTG
GAGTTGCTAGTAACCGCAGGTCAGCATACTGCGGTGAATACGTTCTCGGGCCT
TGTACACACCGCCCGT

Figure 5A

SEQ ID NO 3

```
  1 cagccgccgc ggtaatacgt aggggggcaag cgttatccgg attactgggc gtaaagagg
 61 acgtaggcgg cttcaagt cggatgtgaa atttcccggc tcaaccggga tgagtcattc
121 gatactgttg ggctagagga tagcaggggg agacggaatt cccggtgtag tggttggaata
181 cgtagatacc ggggaggaaca ccagagggcga aggcggtctc caaggctatt tctgacgctg
241 aggtccgaaa gcgtgggtag caaacagact tagatactct ggtagtccac gctgtaaacg
301 atggacacta ggtataggga gcatcgaccc tctttgtgcc gaagctaacg ctttaagtgt
361 cccgcctggg gactacggcc gcaaggctaa aactcaaagg aattgacggg ggcccgcaca
421 agcagcggag cgtgtggttt aattcgatgc aacgcgaaga acctaccaa ggcttgacat
```

Figure 5B

```
481  gtcggaagta gtgaaccgaa aggggaacga cccggttaaa tcggggagccg tcacaggtgc
541  tgcatggctg tcgtcagctc gtgccgtgag gtgtatggtt aagtcctgca acgagcgcaa
601  ccctcgtgcc tagttgaatt ctctagcgag accgccctgc aaaacggggga ggaaggtggg
661  gatgacgtca agtcagcatg gcccttatgc cttgggctac acacacgcta caatgggtgg
721  tacagcaggt agcaataggg taacctggag ctaatcccta aaaccatcct cagttcggat
781  tgtaggctga aactcgcctg catgaagctg gagttgctag taaacgcgta tcagcacggc
841  gcgttgaata cgttttcggg ccttgtacac accgcccgt
```

STIMULATION OF MICROBIAL DECHLORINATION OF POLYCHORINATED BIPHENYLS WITH HALOGENATED ETHENES

CROSS-REFERENCE TO RELATED APPLICATIONS

This application is filed under the provisions of 35 U.S.C. §371 and claims the priority of International Patent Application No. PCT/US03/03202 filed Feb. 3, 2003, which in turn claims priority of U.S. Provisional Patent Application No. 60/353,134 filed on Feb. 1, 2002.

STATEMENT OF GOVERNMENT RIGHTS

The United States Government has rights in this invention under Office of Navel Research Grant Nos. N00014-01-11054 and N00014-01-1-1053.

BACKGROUND OF THE INVENTION

1. Field of the Invention

The present invention relates to compositions and methods for bioremediation of chlorinated biphenyls using dechlorinating microorganisms grown in the presence of stimulating halogenated hydrocarbons, and more particularly, polyhalogenated ethenes.

2. Description of the Related Art

Polychlorinated biphenyls (PCBs) are haloaromatic compounds having exceptional chemical stability. Environmental and toxicological problems caused by the use of PCBs have resulted in restriction of their production under the Toxic Substances Control Act of 1976 and a complete ban of their manufacture by the United States Environmental Protection Agency in 1979. Past disposal practices have resulted in substantial PCB contamination of soils and surface water sediments. As a consequence, in the United States, at least 15% of the PCBs manufactured to date remains in the environment as a highly recalcitrant contaminant. Acute toxicological effects of PCB exposure include chloracne (a skin disease), teratotoxicity, endocrine effects, immunotoxicity, carcinogenicity, and hepatotoxicity (liver damage). The mutagenic and carcinogenic character of PCBs and their suspected role in the reproductive failure of wildlife species are issues of great concern. Further, these compounds bioaccumulate and biomagnify in the fatty tissue of animals in the food web, such as fish, which can affect the human population as a result of food consumption. In sum, the toxicological findings on PCBs and their propensity for bioaccumulation raise concern for the well-being of both humans and wildlife.

Historically, harbor regions have been heavily impacted by the accumulation of polychlorinated biphenyls due to their use in and inadvertent release from naval and industrial applications. Due to their hydrophobic character, PCBs strongly associate with organic carbon, clays and silt that settle into the anaerobic regions of marine sediments.

Although lesser chlorinated PCBs ranging from mono- to hexa-chlorinated congeners can be degraded aerobically, extensively chlorinated congeners (e.g., tetrasubstituted) are not transformed under aerobic conditions. Commercial mixtures of PCBs formerly marketed in the United States under the Aroclor trademark typically contained more than 50 of such extensively-chlorinated congeners. The extent of chlorination of the PCBs varies with the specific commercial mixture. For example, Aroclor 1242 is dominated by tri- and tetrachlorobiphenyls, Aroclor 1260 is dominated by penta-, hexa- and heptachlorobiphenyls, and Aroclor 1268 is dominated by hepta-, octa- and nonachlorobiphenyls. Even less-chlorinated Aroclors contain significant levels of congeners with 5 or more chlorine substituents. For this reason, even a consortium of aerobic bacteria (a consortium being a population of bacteria containing different strains with different congener (degradative) & specificity) cannot remove Aroclor PCB compositions from the environment.

Anaerobic dechlorination of PCBs is a critical step in the biodegradation of these anthropogenic compounds in anaerobic sediments. Thus, in order to completely biodegrade PCBs, both anaerobic and aerobic microorganisms are required since the anaerobic microorganisms dechlorinate more extensively chlorinated PCB congeners recalcitrant to aerobic degradation and only aerobic microorganisms are capable of mineralizing lesser-chlorinated congeners. Knowing which anaerobic microorganisms to stimulate or add to a contaminated sediment or soil was a problem recently solved by the present inventors in copending U.S. patent application Ser. No. 09/860,200, the contents hereby incorporated herein by reference for all purposes.

The present inventors, in U.S. patent application Ser. No. 09/860,200, identified for the first time bacterial catalysts of PCB dechlorination. These PCB dechlorinating bacteria have been designated as bacterium double flank-dechlorinating strain (DF-1) and bacterium ortho-dechlorinating stain (O-17). Both of these microorganisms couple their growth to the dechlorination of PCBs.

Additionally, the present inventors have also identified several other putative PCB dechlorinators that are closely related to DF-1 and O-17. The PCB dechlorinating organisms are phylogenetically most similar, based on 16S rDNA sequence, to *Dehalococcoides* spp. The *Dehalococcoides* spp. bacterium designated CBDB1 has been shown to couple its growth to the dechlorination of chlorobenzenes (Adrian, L. et al. 2000. Nature. 408:580-583), while *Dehalococcoides ethenogenes* couples its growth to the dechlorination of tetrachloroethene (Maymo-Gatell, X. et al. 1997. Science. 276:1568-1571), Both chlorobenzenes and tetrachloroethene have been listed by the U.S. EPA as priority pollutants.

Stimulation of the growth and PCB dechlorinating activity of these organisms is required in order to initiate and sustain good biodegradation of PCBs. Due to this limitation investigators have searched for suitable stimulating agents. PCBs (Wu, Q. et al., 1997. Appl. Environ. Microbiol. 63:4818-4825), polybrominated biphenyls (Wu, Q. et al., 1999. Environ. Sci. Technol. 33:595-602; U.S. Pat. No. 5,227,069), halogenated benzoic acids and halogenated salicylic acids (U.S. Pat. No. 5,484,729) have all been shown to stimulate the microbial dechlorination of PCBs when added to sediments. However, these methods have not been proven suitable for all applications. This is in part due to i) inadequate (limited) stimulation, ii) the application of stimulating agent being environmentally undesirable or iii) the stimulant remaining in the sediment after treatment. Thus, there is a need to in the art for compositions and methods that stimulate degradation of PCBs without the negative side-effects presently known to exist.

SUMMARY OF THE INVENTION

This invention relates in one aspect to a method for anaerobic microbial dechlorination of polychlorinated biphenyls (PCBs) that can be coupled with aerobic degradation of PCBs, the method comprising contacting PCB dechlorinating bacteria with an effective amount of a stimulant to increase dechlorination activity, wherein the stimulant comprises at least one polyhalogenated ethene.

Preferably, the PCB dechlorinating bacteria comprise DF-1 and O-17, as described in U.S. patent application Ser. No. 09/860,200. DF-1 and O-17 have been identified as microorganisms that dechlorinate PCBs and chlorobenzenes and the first identification of an organism that would dechlorinate chlorobenzenes with more than 4 chlorines. Additionally the bacteria DF-1 and O-17 dechlorinate not only tetrachloroethene but also PCBs. While tetrachloroethene is a substrate of *D. ethenogenes*, the prior art does not teach or suggest that *D. ethenogenes* has PCB dechlorinating activity or that tetrachloroethene would stimulate any PCB dechlorinating activity in the bacterium.

Advantageously, the DF-1 and O-17 bacteria have the ability to essentially completely consume tetrachloroethene via sequential reductive dechlorination steps to trichloroethene (TCE), trans-, cis- and 1,1-dichloroethene (DCEs), vinyl chloride (VC) and finally ethene. All of the intermediate compounds of the reaction have been identified, with all of them being volatile compounds. Analysis of the cultures indicates that DF-1 and O-17 couple their growth to the dechlorination of tetrachloroethene. When combined, PCBs and tetrachloroethene were simultaneously dechlorinated and tetrachloroethene did not inhibit or significantly delay PCB dechlorination, demonstrating another advantage of using tetrachloroethene as a stimulant.

PCBs are soluble in tetrachloroethene and tetrachloroethene is partially soluble in water (up to 1 mM). PCBs are frequently unavailable to microorganisms due to their sequestration in the organic components of the sediment. Using tetrachloroethene as the stimulatory agent for dechlorination, results in the application of a solvent that solubilizes PCBs thereby allowing improved contact between the PCBs and the PCB dechlorinating bacteria. This makes "aged" PCBs more bioavailable to PCB dechlorinating microbes. Furthermore, the solubilization of PCBs by organic stimulants enhances the bioavailability of the PCBs to aerobic bacteria.

Additionally, other compounds that can serve as stimulants of PCB dechlorination in bacteria that also have the added benefit of solubilizing PCBs, include but are not limited to, trichloroethene and dichloroethene. Other applicable compounds include carbon tetrachloride, methylene chloride, chloroform, any chlorinated fluorocarbon, tetrachloroethane, trichloroethanes, trichlorobenzenes and chlorinated propenes. Several of these compounds are also volatile or can be easily volatilized, aiding in their removal.

In another aspect, the present invention relates to a method for stimulating PCB dechlorination comprising contacting bacteria strains DF-1 and/or O-17 with an effective amount of a polyhalogenated ethane to stimulate the growth and/or PCB dechlorinating activity of the DF-1 and/or O-17 bacteria strains.

In yet another aspect, the present invention relates to a method for dechlorinating PCBs, the method comprising:
 placing soil or sediment comprising PCBs in a container, preferably, a closable container;
 introducing into the container for contacting with the soil or sediment an effective amount of a stimulant of PCB dechlorinating bacteria, wherein the stimulant comprises at least one polyhalogenated ethene;
 incubating the soil or sediment in the container for a sufficient time to reduce PCBs in the soil or sediment.

Preferably the soil or sediment has included therein the PCB dechlorinating bacteria DF-1 or O-17 and the polyhalogenated ethene is tetrachloroethene. The PCB dechlorinating bacteria may be added before, after or simultaneously with the inclusion of the stimulant.

In still another aspect, the present invention relates to a method for dechlorinating PCBs, comprising:
 placing soil or sediment comprising PCBs in a container, preferably, a closable container; wherein the soil or sediment comprises at least one PCB dechlorinating bacteria;
 introducing into the container for contact with the soil or sediment an effective amount of a stimulant of PCB dechlorinating bacteria, wherein the stimulant comprises at least one polyhalogenated ethene;
 incubating the soil or sediment in the container for a sufficient time to reduce PCBs in the soil or sediment;
 purging the container with air to remove volatile compounds;
 purging the container with air or oxygen to stimulate aerobic PCB degrading bacterial; and
 incubating and aerating the soil or sediment to allow for degradation of the PCBS.

PCB dechlorinating bacteria, that being aerobic and/or anaerobic may be added before, after or simultaneously with the inclusion of the stimulant. Preferably the soil or sediment has included therein the PCB dechlorinating bacteria DF-1 or O-17 and the polyhalogenated ethene is tetrachloroethene.

There are several advantages of using tetrachloroethene as a stimulatory agent of microbial PCB dechlorination: 1) tetrachloroethene stimulates the growth and dechlorination of PCB dechlorinating bacteria; 2) tetrachloroethene and PCBs are dechlorinated simultaneously; 3) PCBs are soluble in tetrachloroethene and tetrachloroethene is water-soluble thereby enhancing the bioavailability of PCBs; 4) tetrachloroethene is biodegradable; 5) tetrachloroethene and all of its dechlorination products are both water-soluble and volatile and therefore are removable from the environment; 6) tetrachloroethene is readily available and inexpensive; and 7) tetrachloroethene provides a practical substrate for mass culturing PCB dechlorinating microbes, which can serve as an inoculum for reactor systems.

Other aspects, features and embodiments of the invention will be more fully apparent from the ensuing disclosure and appended claims.

BRIEF DESCRIPTION OF THE DRAWINGS

FIG. 2 is a diagram of the PCB degrading process.

DETAILED DESCRIPTION AND PREFERRED EMBODIMENTS OF THE INVENTION

As used herein, the following terms shall have the following meanings:

"PCB dechlorinating bacteria" means bacteria that metabolize PCBs by dechlorination. These bacteria are found in the environment and as isolated cultures.

"Stimulating PCB dechlorinating bacteria" means increasing the rate of growth of PCB dechlorinating bacteria and/or increasing the dechlorinating activity of PCB dechlorinating bacteria.

"Stimulant" means a compound which, when contacted with PCB dechlorinating bacteria, increases the rate of growth of PCB dechlorinating bacteria and/or increases the dechlorinating activity of PCB dechlorinating bacteria.

"Growth" means an increase in the size and/or quantity of the bacteria.

"Effective amount of a stimulant" means an amount of stimulant that will increase the rate of growth of PCB dechlorinating bacteria and/or increase the dechlorinating activity of PCB dechlorinating bacteria.

Described is an improved process for anaerobic microbial dechlorination of polychlorinated biphenyls (PCBs) in sediments or soil. At least one polyhalogenated ethene is added as a stimulating agent, which enhances the growth and/or dechlorinating activity of PCB dechlorinating bacteria. The residual polyhalogenated ethene and catabolic products are further biodegraded or trapped in an off-gas. The dechlorinated PCBs are mineralized through the action of aerobic bacteria stimulated by oxygen introduced into the reactor.

The compositions and methods of the invention may be employed to biodegrade halogenated organic waste, e.g., contaminated soil from landfill sites, river beds, etc., containing PCBs, as well as to treat leachates and aqueous surfactant solutions resulting from washing the aforementioned organic waste to transfer PCBs to the aqueous surfactant solutions. Surfactants potentially useful for such purpose of washing contaminated organic wastes include alkylbenzene sulfonate surfactants, e.g., Surco 233 (Onyx Chemical Co., Jersey City, N.J.), a sodium salt of an alkylbenzene sulfonate.

The invention contemplates treatment of a PCB-containing environment by inoculation or other introduction of microbially effective agents of the invention to the environment. For example, dechlorinating bacteria in accordance with the invention may be dispersed on a landfill site under appropriate conditions for effective biodegradative action on PCBs in the environment. Such dispersant may include the microbial agent in a nutrient medium, particularly if the PCB-containing environment is nutrient-deficient for such microbial species. The level of biodegradation of the PCBs can be monitored continuously or intermittently to determine the effectiveness of the microbial treatment.

The dechlorination/bioremediation processes of the present invention may if desired be advantageously combined with other bioremediation and waste-degradation methods conventionally employed in the art, to achieve an enhanced decontamination or purification result. The methods of the following U.S. patents, herein incorporated by reference in their entireties, are illustrative: U.S. Pat. No. 5,968,360 (composition and method for degradation of polychlorinated biphenyls in soil), U.S. Pat. No. 5,635,393 (method for dechlorinating polychlorinated biphenyls and granules for use therein), U.S. Pat. No. 5,618,727 (bioremediation process design utilizing in situ soil washing), U.S. Pat. No. 5,540,838 (stimulation of microbial para-dechlorination of polychlorinated biphenyls), U.S. Pat. No. 4,876,201 (method for biodegrading PCBs), U.S. Pat. No. 5,932,472 (method for degradation of polychlorinated biphenyls in soil), U.S. Pat. No. 5,858,692 (polychlorinated biphenyls (PCB) immunoassay method, its components and a kit for use in performing the same), U.S. Pat. No. 5,834,222 (polychlorinated biphenyls (PCB) immunoassay method, its components and a kit for use in performing the same), U.S. Pat. No. 5,750,065 (adsorption of PCBs using biosorbents), U.S. Pat. No. 5,242,601 (sludge treatment with CaO or $CaC_2$ and recovery of CaO therefrom), and U.S. Pat. No. 4,950,309 (process for the conversion of toxic organic substances to useful products).

The compositions and methods of the invention may be employed for anaerobically degrading extensively chlorinated congeners to primarily mono- and dichlorobiphenyls, e.g., involving the treatment of PCBs with an anaerobic consortium of bacteria in accordance with the invention, followed by treatment with an aerobic consortium of bacteria, to maximize the overall degradation of PCBs.

The invention therefore contemplates the treatment of highly chlorinated PCBs by an anaerobic consortium of microbial species (species that are anaerobically effective for dechlorination of the highly chlorinated congeners), followed by treatment of the correspondingly anaerobically degraded PCBs with an aerobic consortium of microbial species (that are aerobically effective for dechlorination of the partially degraded PCBs).

Such treatment may for example be conducted at a PCB-containing site, e.g., including water, soil and/or sediment, or otherwise with respect to a separated or recovered PCB-containing material or isolated PCBs, in which one or more PCB-degrading anaerobic microorganisms is brought into degradative relationship with the PCB(s) to effect at least partial dechlorination of the PCB(s) under conditions effective for such microbial action. The dechlorinating action may include removal of chlorine substituents from the ortho position of a ring of the PCB, and/or removal of chlorine substituents that are double-flanked by other chloro substituents on the biphenyl ring structure. The microbial consortia employed for such purpose may further contain or be followed in the treatment flow sequence by organisms specifically adapted for dechlorination of para- and meta-chloro substituents, to provide a comprehensive dechlorination treatment of the PCB(s).

Figure 1:
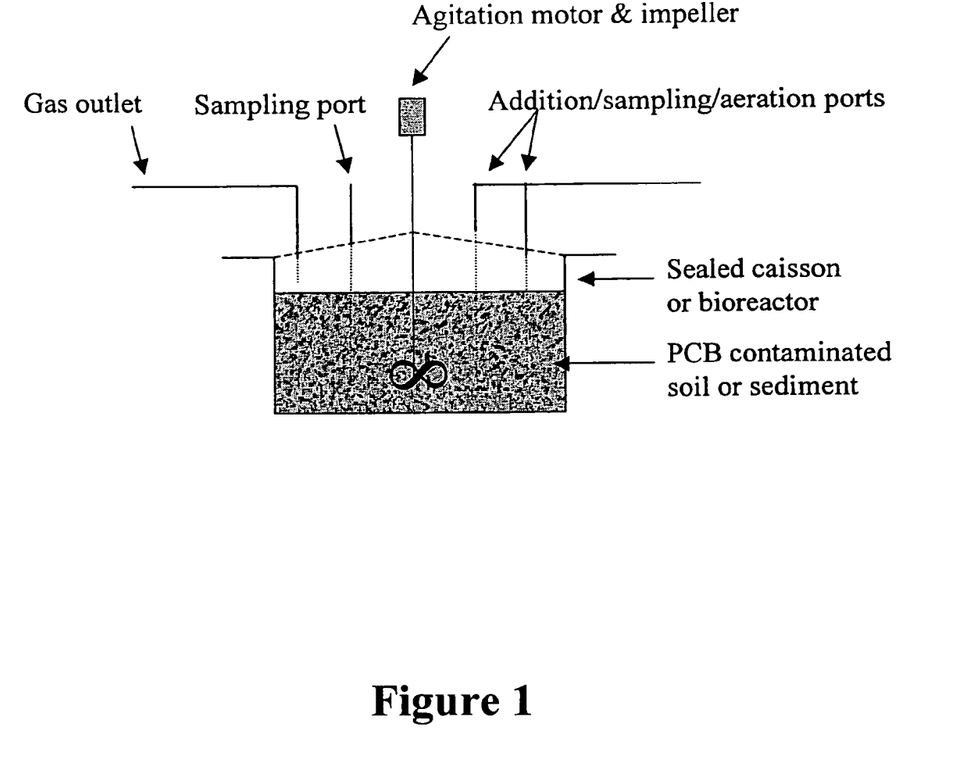
FIG. 1 is a diagram of a bioreactor for treatment of PCB contaminated soils and sediments using tetrachloroethene as a stimulant.
Figure 2A:
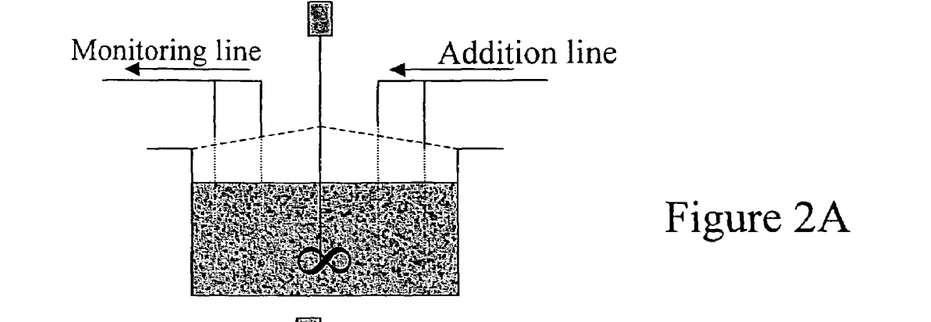
FIG. 2A: Phase 1, sealed bioreactor or caisson with PCB contaminated soils or sediments are set up.
Figures 2B, 2C:
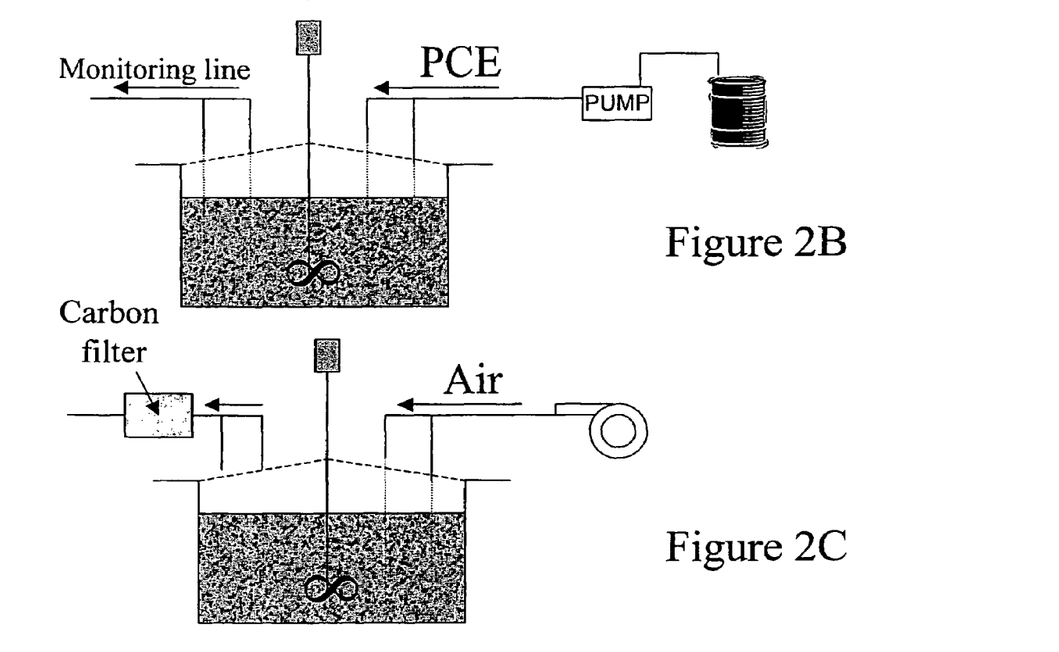
FIG. 2B: Phase 2, tetrachloroethene and/or tetrachloroethene containing soil is added to the soil or sediment slurry. Slurry is mixed and incubated to stimulate dechlorination of PCBs.
FIG. 2C: Phase 3, system is purged with air to strip out volatiles. System is either purged with air or oxygen-generating chemicals are pumped in to stimulate aerobic PCB degraders. Slurry is incubated with continued aeration to degrade PCBs.
Figure 2D:
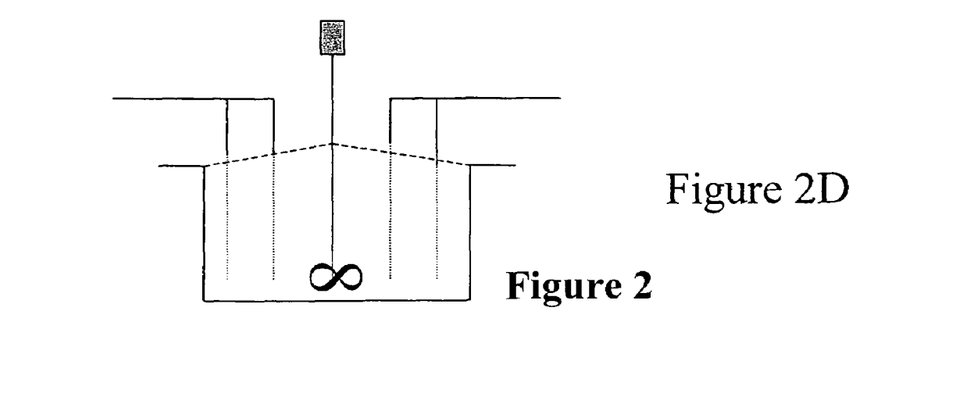
FIG. 2D: Phase 4, treated soil/sediment is removed and used as clean fill. The cycle is repeated with contaminated soil/sediment.
Figure 3A:
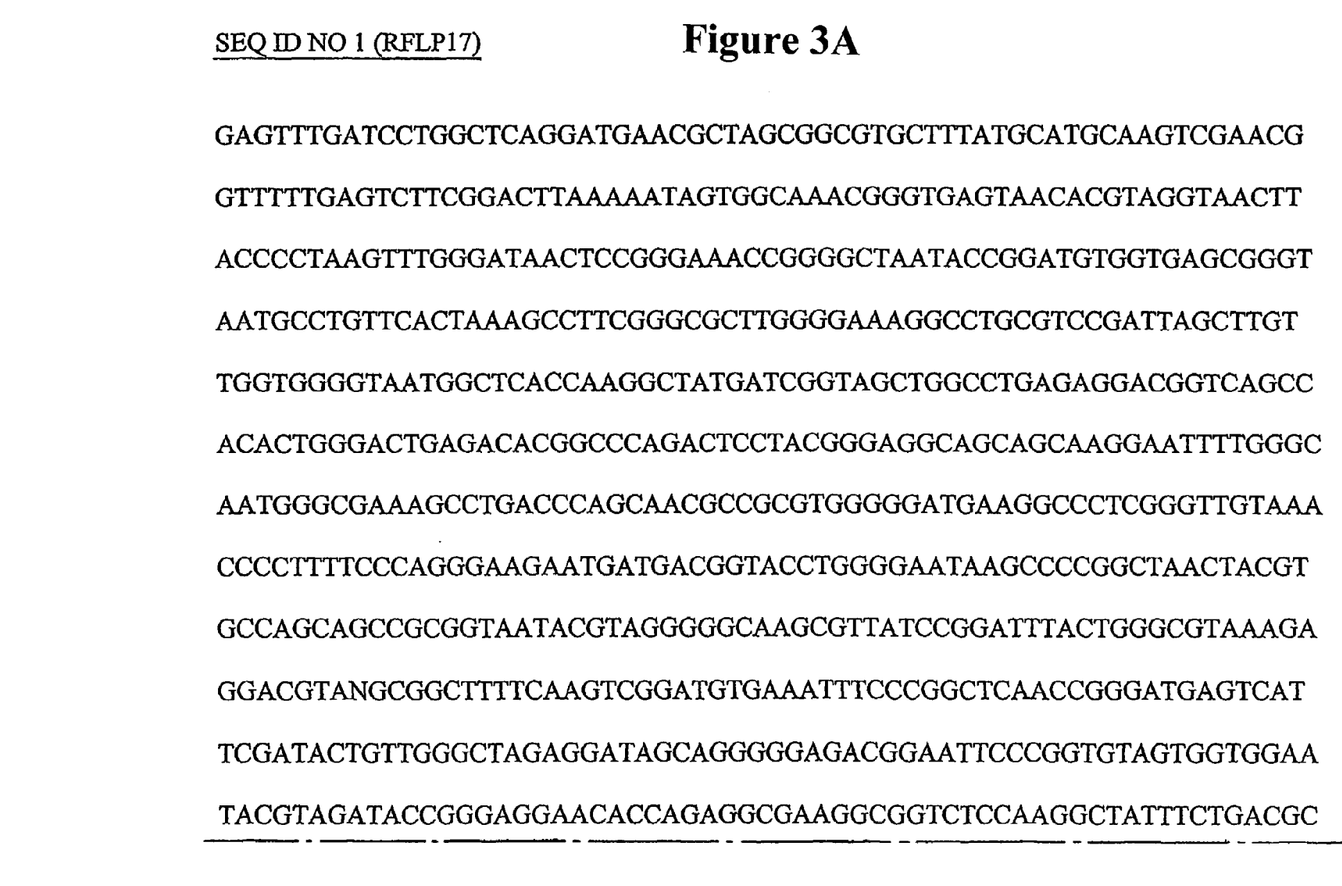
FIG. 3 is a depiction of SEQ ID NO. 1.
Figure 3B:
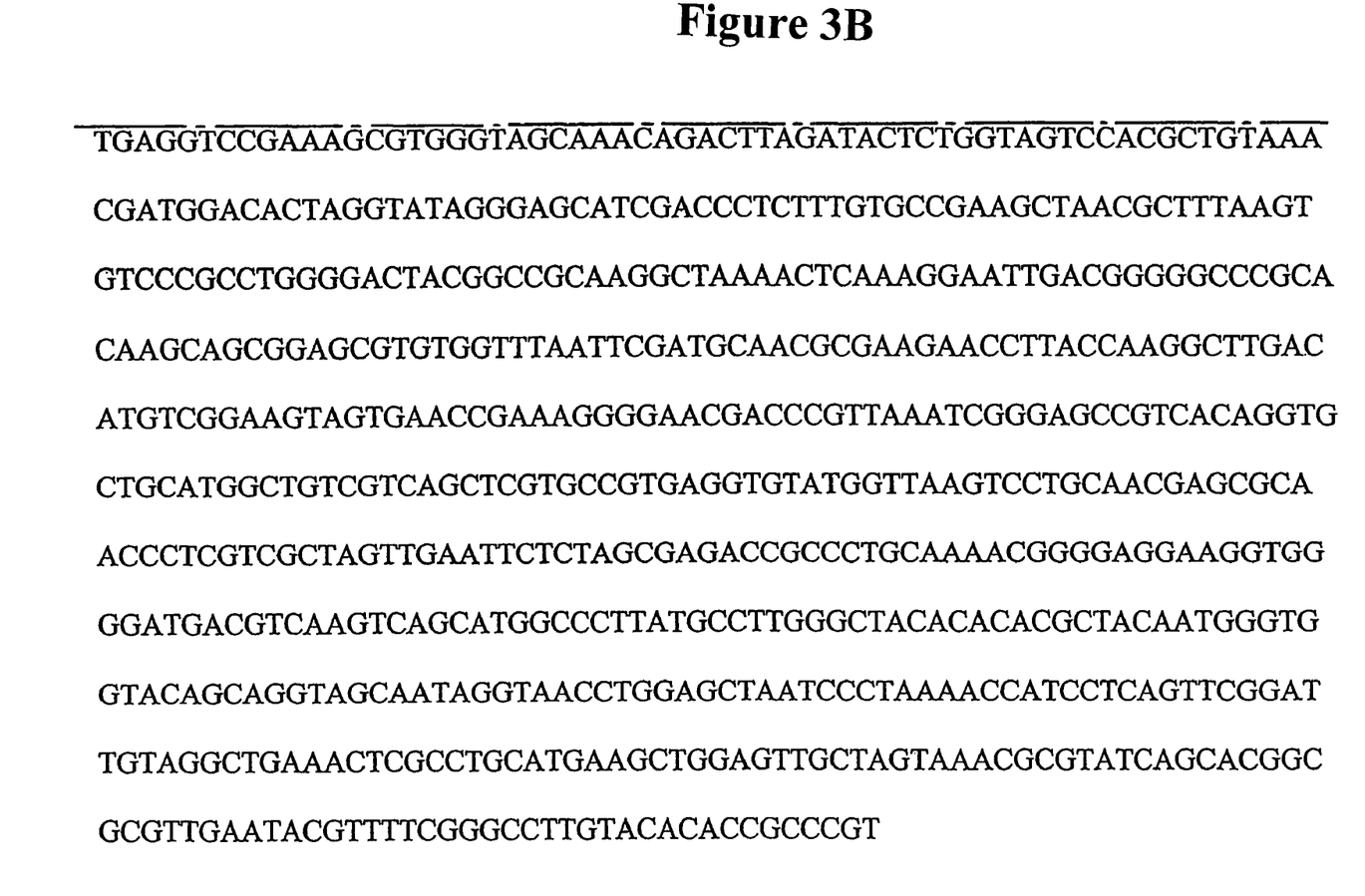
Figure 4:
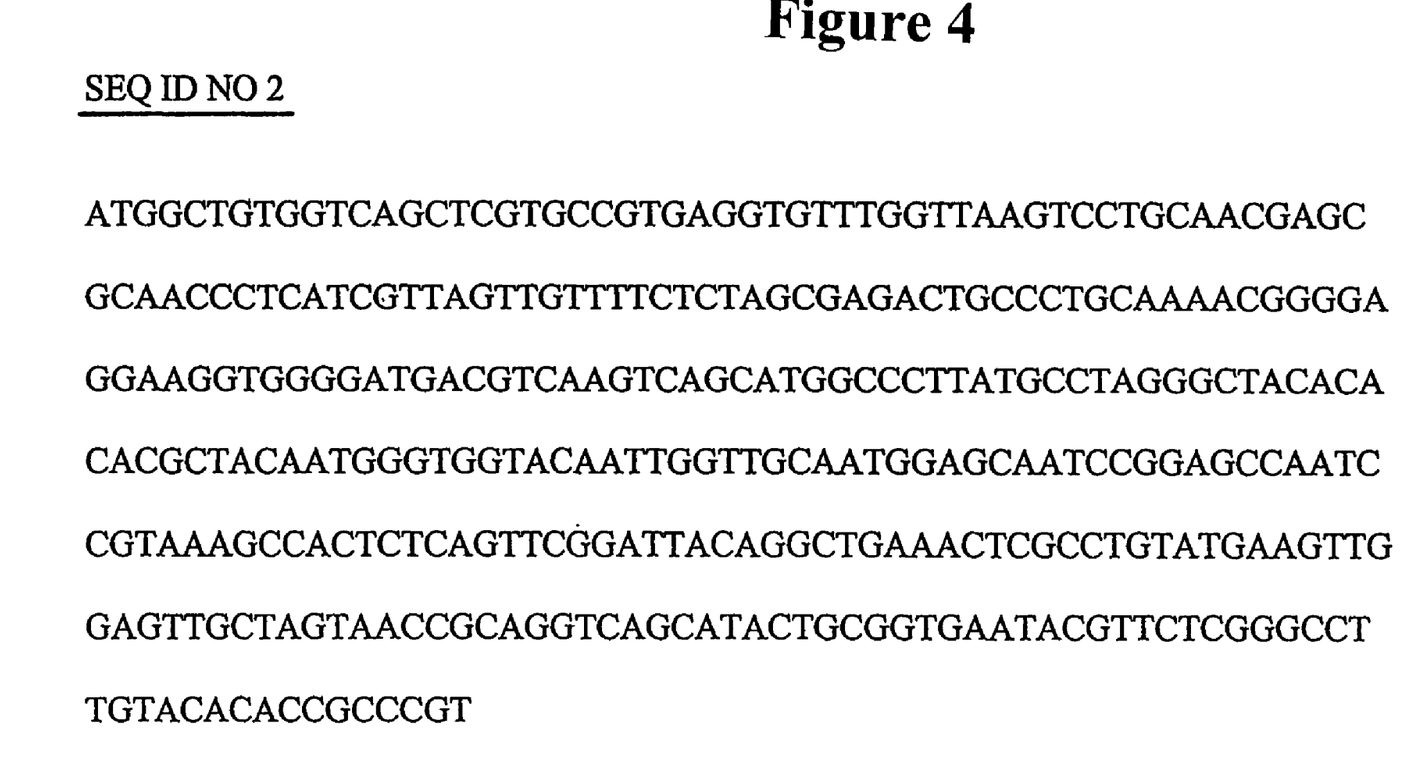
FIG. 4 is a depiction of SEQ ID NO. 2.
Figure 5A:
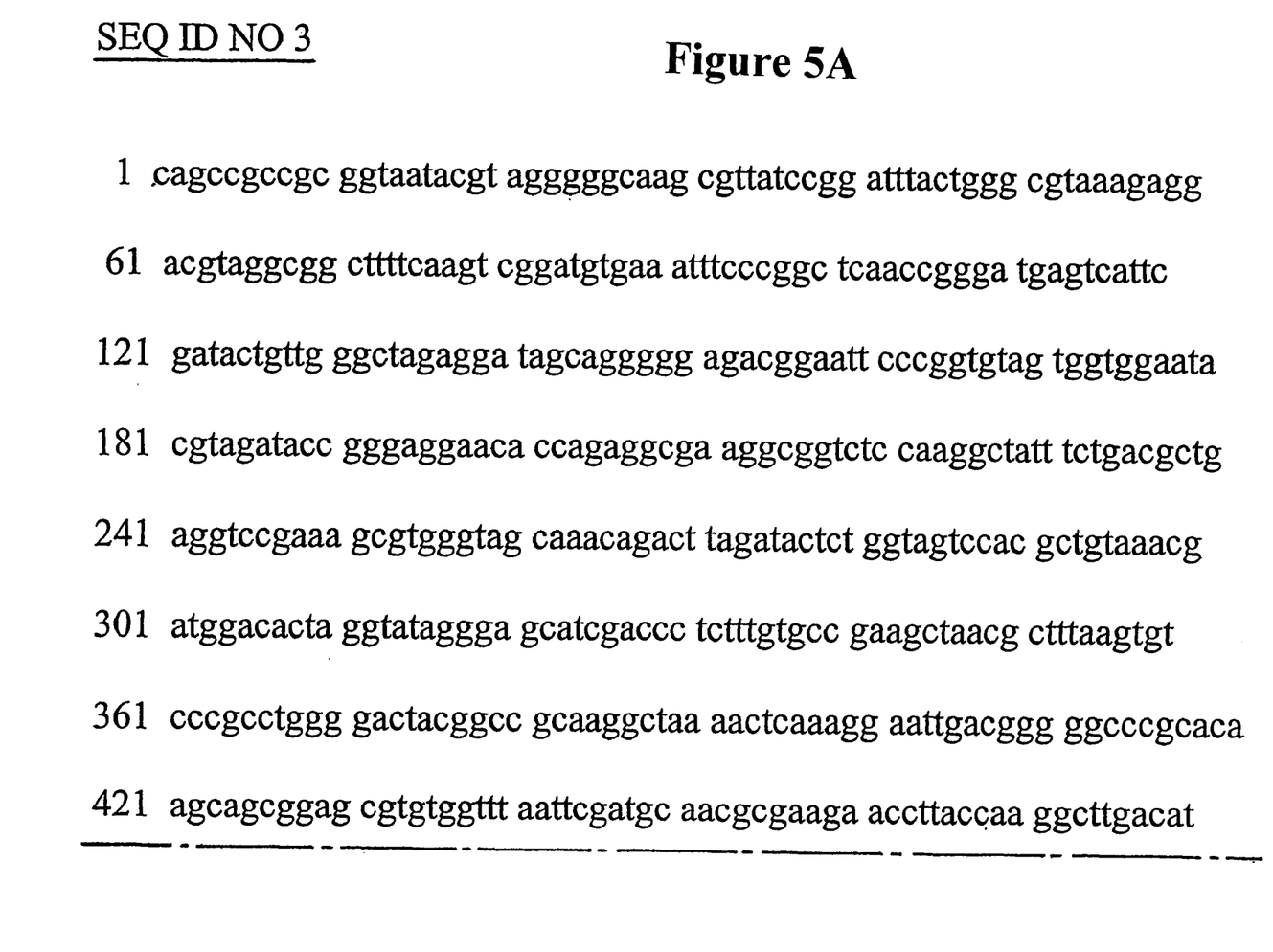
FIG. 5 is a depiction of SEQ ID NO. 3.
Figure 5B:
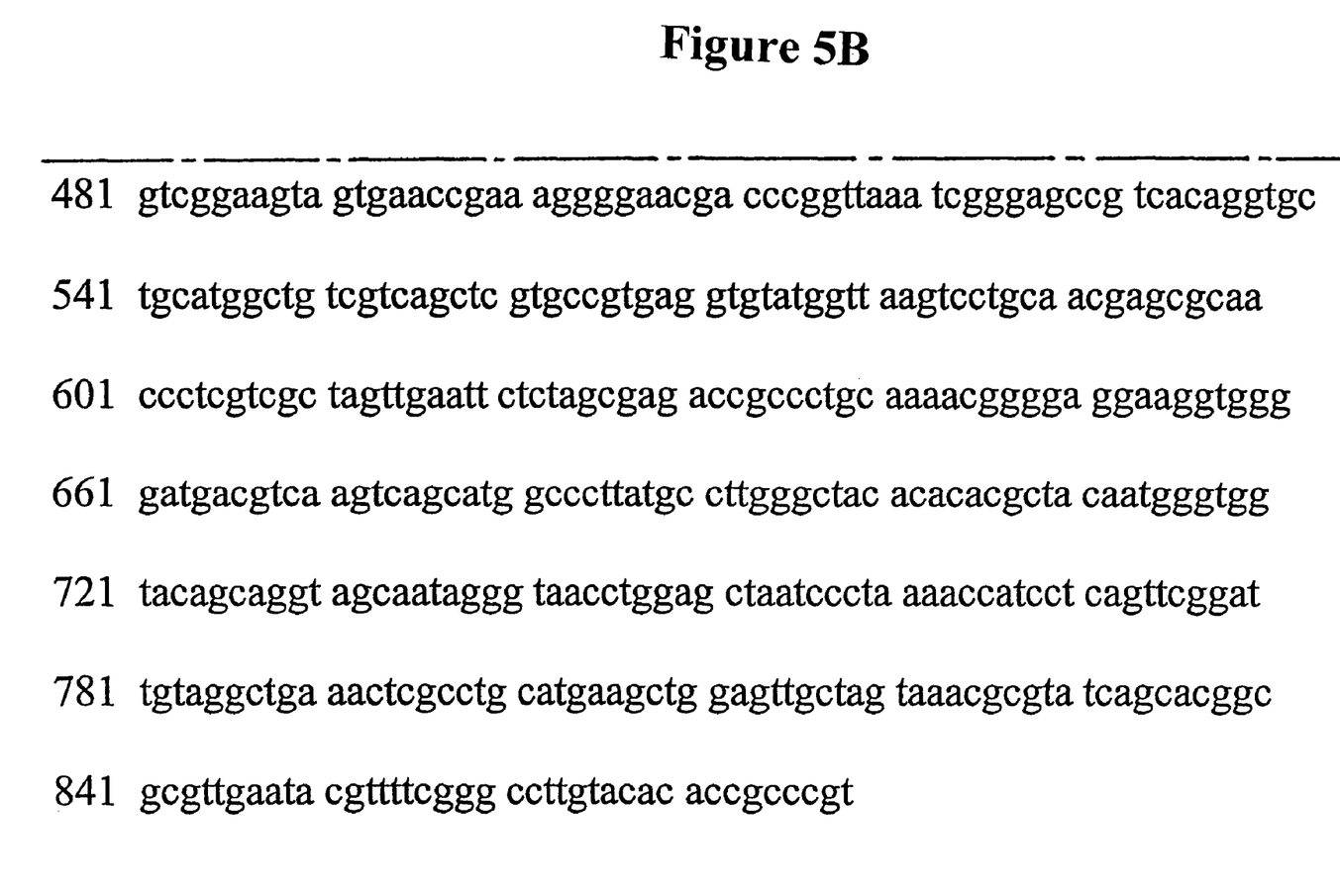
Figure 6:
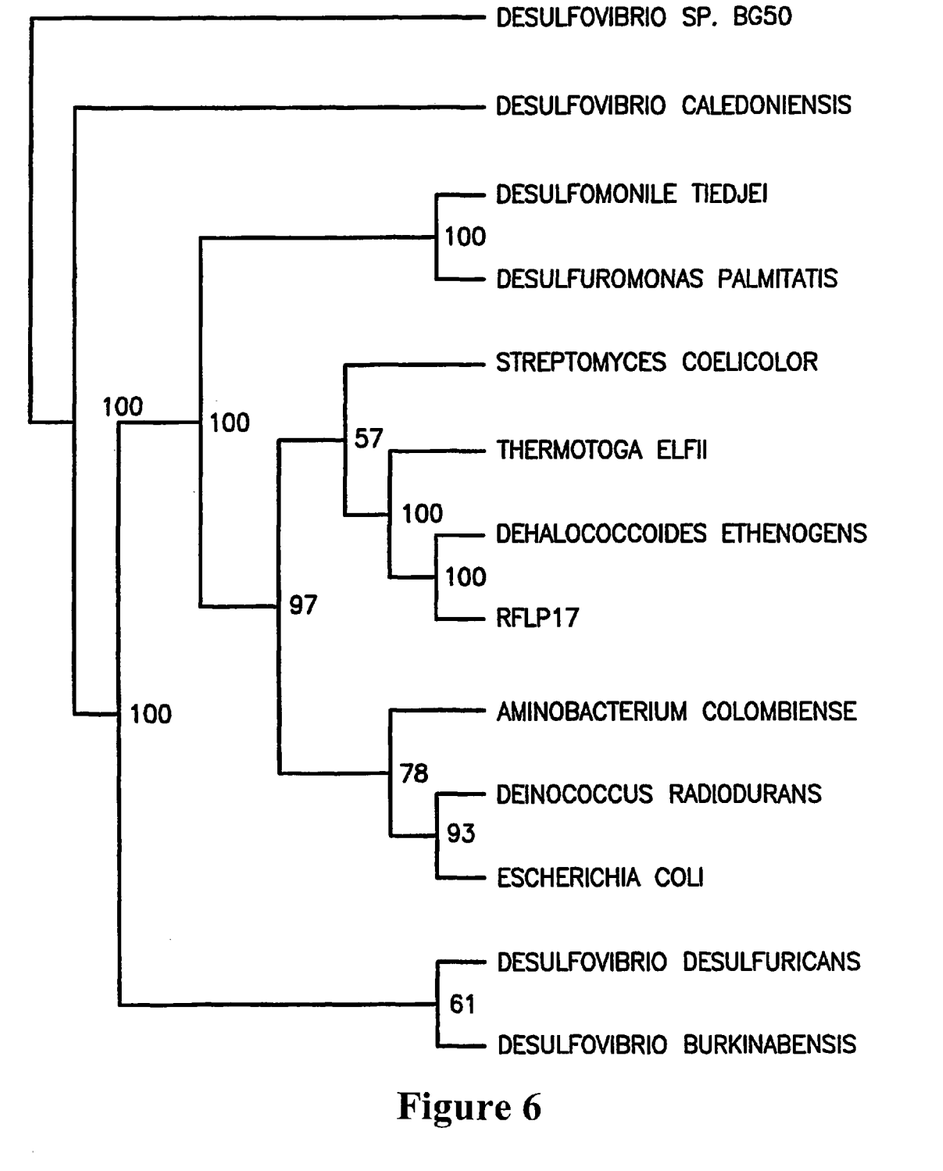
FIGS. 6 and 7 are phylogenetic charts of microbial species including species advantageously employed in the practice of the present invention.
Figure 7:
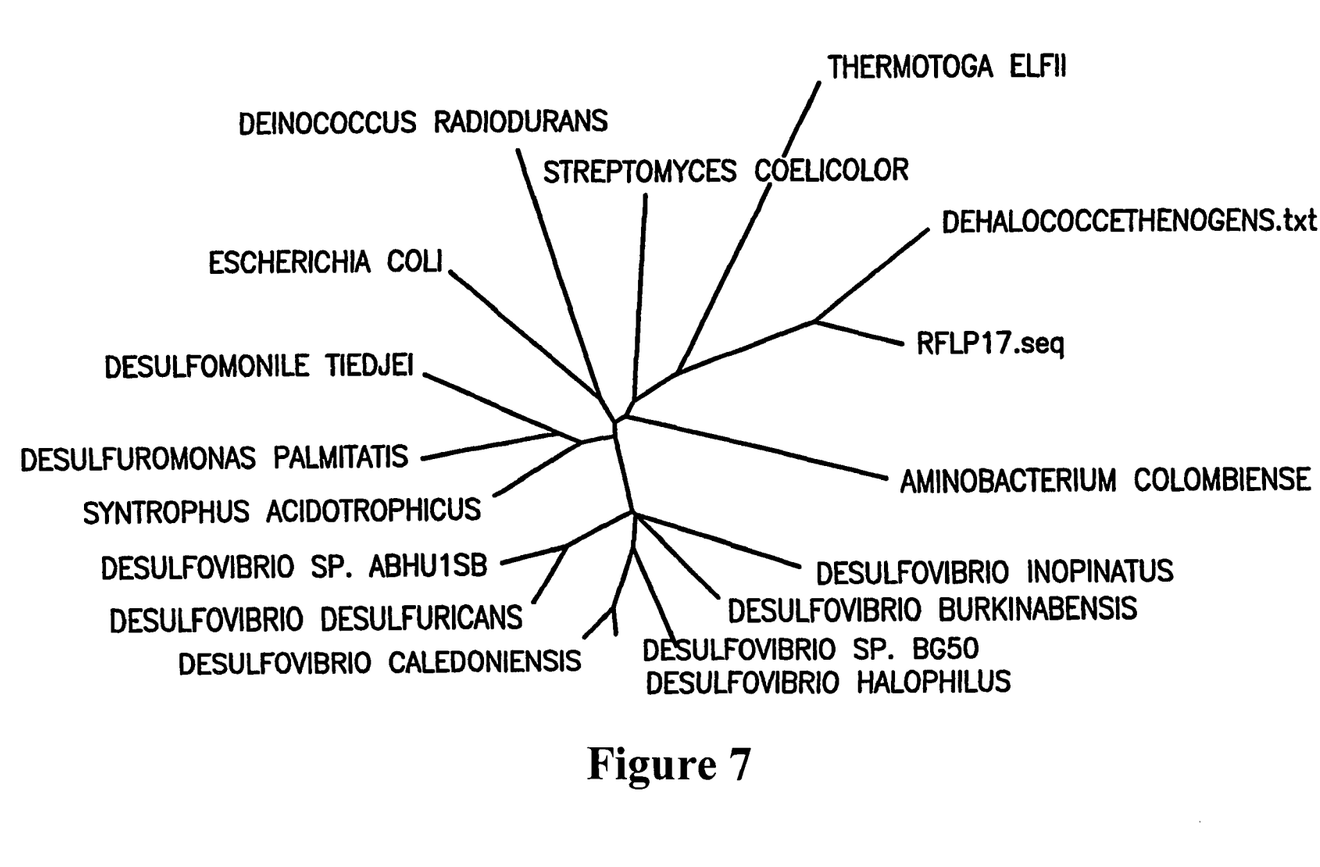

A cultured PCB dechlorinating bacteria may be used in the method of dechlorination of polychlorinated biphenyls. Preferably, PCB dechlorinating bacteria potentially useful in the consortia employed for PCB dechlorination include those in the phylogenetic depictions of FIGS. 6 and 7. More preferably, the PCB dechlorinating bacteria species comprises a 16S ribosomal subunit nucleic acid sequence selected from the group consisting of:

(a) a nucleic acid sequence that has more than 95% identity, and preferably more than 98% identity, to a nucleic acid sequence selected from the group consisting of SEQ ID NO 1, SEQ ID NO 2, and SEQ ID NO 3 wherein the quantitative identity is readily determinable, e.g., by use of a DNAsis computer program and default parameters;

(b) a nucleic acid sequence fully complementary to a nucleic acid of (a).

The invention in specific embodiments utilize dechlorinating compositions comprising strain O-17 (a sequence having 100% identity to SEQ ID NO 3) and/or strain DF-1 (a sequence having 89% identity to SEQ ID NO 3), where these strains may be present singly, or alternatively in a consortium of microbial strains of diverse character having corresponding activity for dechlorination of variant PCB congener structures.

The present invention further includes stimulating agents of PCB dechlorinating bacteria that includes organic compounds that solubilize PCBs, can be volatize and enhance the bioavailability of the PCBs to aerobic bacteria. Non-limiting examples of stimulating agents that may be used in the practice of the invention include polyhalogenated ethenes, as for example may be added to the chlorinated biphenyl-containing environment being treated. For example, dechlorination may be carried out under sufficient conditions to effect dechlorination of flanked chlorine of poly-chlorinated biphenyl present in the environment being treated by the microbial species, utilizing appropriate additives/growth conditions.

Tetrachloroethene and related polyhalogenated ethenes are used to stimulate the growth and dechlorinating activity of PCB dechlorinating bacteria in a contaminated soil or sediment. Due to the volatility of tetrachloroethene, adding to a closed system minimizes dispersal of the tetrachloroethene from the treated medium. The process of dechlorinating PCBs is performed in an enclosed system such as a caisson, which is introduced into river, pond, lake or harbor sediments. Alternatively the PCB contaminated material is excavated from soil or river, pond, lake or harbor sediments and placed into an enclosed reactor. This approach is also used to mass culture PCB dechlorinating microorganisms for use as an inoculum in PCB dechlorination treatment reactors. This process is scaled according to the amount of PCB contaminated soils and sediments to be treated.

Stimulants of PCB dechlorinating bacteria are polyhalogenated ethenes. Polyhalogenated ethenes include ethenes comprising from two to four halogen groups, where the halogen groups are all identical, all different or any combination of two to four halogen groups. Examples of polyhalogenated ethenes include but are not limited to tetrachloroethene, trichloroethene, trans- and cis-dichloroethene, 1,1-dichloroethene, tetrabromoethene, tribromoethene, trans- and cis-dibromoethene, 1,1-dibromoethene, tetraiodoethene, triiodoethene, trans- and cis-diiodoethene, 1,1-diiodoethene, tetrafluoroethene, trifluoroethene, trans- and cis-difluoroethene, 1,1-difluoroethene, trans- and cis-dibromochloroethene, 1,1-dibromochloroethene, trans- and cis-dichlorobromoethene, 1,1-dichlorobromoethene, trans- and cis-diiodochloroethene, 1,1-diiodochloroethene, trans- and cis-dichloroiodoethene, 1,1-dichloroiodoethene, trans- and cis-difluorochloroethene, 1,1-difluorochloroethene, trans- and cis-dichlorofluoroethene, 1,1-dichlorofluoroethene, trans- and cis-dibromoiodoethene, 1,1-dibromoiodoethene trans- and cis-diiodobromoethene, 1,1-diiodobromoethene, trans- and cis-dibromofluoroethene, 1,1-dibromofluoroethene, trans- and cis-difluorobromoethene, 1,1-difluorobromoethene, trans- and cis-diiodofluoroethene, 1,1-diiodofluoroethene, trans- and cis-difluoroiodoethene and 1,1-difluoroiodoethene.

Stimulants of PCB dechlorinating bacteria also include carbon tetrachloride, methylene chloride, chloroform, any chlorinated fluorocarbon, tetrachloroethane, trichloroethanes, trichlorobenzenes, chlorinated propenes and any ethenically unsaturated species. Examples of chlorinated fluorocarbons include but are not limited to trichlorofluoromethane, trichlorotifluoroethane, dichlorodifluoromethane, dichlorotetrafluoroethane and chloropentafluoroethane. Examples of chlorinated propenes include but are not limited to chloropropene, dichloropropene, trichloropropene, tetrachloropropene and pentachloropropene.

A preferred embodiment of the invention is a method for stimulating PCB dechlorinating bacteria comprising contacting PCB dechlorinating bacteria with an effective amount of a stimulant, wherein the stimulant comprises at least one polyhalogenated ethene.

The stimulant may include a final total concentration of polyhalogenated ethene(s) of from about 1 µM to about 100 mM, preferably from about 5 µM to about 50 mM, more preferably from about 100 µM to about 1 mM, and most preferably from about 50 µM to about 0.5 mM.

Further the invention includes the addition of a polyhalogenated ethene to a medium for culturing PCB dechlorinating bacteria such that the final total concentration of polyhalogenated ethene(s) is from about 1 µM to about 100 mM, preferably from about 5 µM to about 50 mM, more preferably from about 100 µM to about 1 mM, and most preferably from about 50 µM to about 0.5 mM.

Yet a further embodiment of the invention includes the addition of a polyhalogenated ethene and at least one other compound selected from the group comprising carbon tetrachloride, methylene chloride, chloroform, any chlorinated fluorocarbon, tetrachloroethane, trichloroethanes, trichlorobenzenes and chlorinated propenes to a sediment such that the final total concentration of polyhalogenated ethene(s) is preferably from about 1 µM to 100 mM, preferably from about 5 µM to 50 mM, more preferably from about 100 µM to about 1 mM, and most preferably from about 50 µM to 0.5 mM and the final total concentration of said other compound (s) is from about 1 µM to 100 mM, preferably from about 5 µM to 50 mM, more preferably from about 100 µM to about 1 mM, and most preferably from about 50 µM to 0.5 mM.

The invention enables the effective dechlorination of chlorinated biphenyls, involving the provision in the chlorinated biphenyl-containing environment of growth conditions for the microorganism(s) such that chlorine is at least partially removed from the chlorinated biphenyl. The features and advantages of the invention are more fully apparent from the following illustrative examples, which are not intended in any way to be limitingly construed, as regards the invention hereinafter claimed.

EXAMPLE 1

Tetrachloroethene is used to stimulate the growth and dechlorinating activity of PCB dechlorinating bacteria in a contaminated soil or sediment. Due to the volatility of the tetrachloroethene, tetrachloroethene works best when added to a closed system. For contaminated sediments, such a closed system comprises a caisson that is lowered into the sediment of a lake, river, pond or harbor. If needed, the bottom of the caisson is closed after introduction into the sediment, with the bottom of the caisson located well below the contaminated sediment. The top is enclosed with several sampling and addition ports that extend into the sediment or aqueous headspace. An impeller shaft is run down the middle of the caisson to allow mixing of the sediment. Ports for sampling of the sediment and water are present, allowing PCB and tetrachloroethene analysis. Nutrients (energy sources and fertilizers if needed) and gasses are introduced through such sealable ports. The tetrachloroethene is added at levels ranging from 100 µM to at least 1 mM and then mixed with the sediment. If necessary, anaerobic PCB dechlorinating bacteria is added to the sediment. 16S rDNA probes (U.S. patent application Ser. No. 09/860,200) are used to monitor this microbial population before and after introduction of PCB dechlorinating bacteria. Once dechlorination of extensively chlorinated PCBs to tri-, di- and mono-chlorinated biphenyls is complete, volatile ethene and any residual tetrachloroethene and partially dechlorinated intermediates TCE, DCEs and VC are sparged out of the caisson by the introduction of nitrogen gas or air. The tetrachloroethene and its volatile dechlorination products are trapped in a carbon-containing trap. At this stage the system is made aerobic by the introduction of air, oxygen or an oxygen-containing compound such as hydrogen peroxide. If needed, aerobic PCB degrading bacteria are introduced into the system to complete the degradation of the PCBs to carbon dioxide. Such aerobic PCB degrading bacteria are readily available (U.S. Pat. No. 5,897,996; Seeger, M. et al., 2001. J. Bacteriol. 183(12):3548-3555; Megharaj, M. et al., 1998. Appl. Microbiol. Biotechnol. 49(3):337- 342). The dechlorinating activity of the PCB degrading bacteria and the amount of these bacteria is monitored using molecular probes. Tetrachloroethene may be substituted in the described method with any polyhalogenated ethene.

EXAMPLE 2

An alternative to an in situ caisson is a fixed or portable reactor. Dredge material or excavated soil is added to a reactor or lined impermeable basin on-site or delivered to the reactor or lined impermeable basin at an off-site location. The system remains closed, with several sampling and addition ports extending into the soil or sediment. Bulk carbon & energy sources are introduced to make the system anaerobic. Nitrogen and carbon dioxide gases are used to promote anaerobiosis. Tetrachloroethene is introduced into the system to promote PCB dechlorination and the remaining process is as described for Example 1. The system is vented through a carbon trap to capture any volatile compounds.

EXAMPLE 3

Tetrachloroethene is used to develop cell material for PCB dechlorination. PCB dechlorination species are mass cultured in a closed bioreactor using tetrachloroethene as a substrate. Since tetrachloroethene is partially soluble in water, more substrate is available to the culture. Tetrachloroethene degradation is monitored by gas chromatography while tetrachloroethene is added to the culture as it becomes depleted, with either continuous or batch additions of tetrachloroethene. Tetrachloroethene is added at a concentration sufficient to maintain the growth of PCB dechlorinating bacteria. Once the culture has attained maximum cell density, residual tetrachloroethene and its intermediates are purged from the system with nitrogen. The cells are then harvested using conventional continuous centrifugation or filtration methods. Concentrated cell material is diluted in a buffer and then used as an inoculum in PCB treatment systems. Preferably the polyhalogenated ethane is tetrachloroethene.

EXAMPLE 4

Culture Conditions. A sterile media was prepared composed of at least one of the following components in grams per liter (final concentration) of demineralized water: $Na_2CO_3$, 3.0; $Na_2HPO_4$, 0.6; $NH_4Cl$, 0.5; cysteine-$HCl.H_2O$, 0.25; $Na_2S.9H_2O$, 0.25; resazurin, 0.001. In addition, 1% (v/v) each of vitamin and trace element solutions was added. An anaerobic enrichment culture comprising either O-17 (GenBank Accession #: AF058005; Appl Environ Microbiol. 1998 September; 64(9):3359-67)or DF-1 (GenBank Accession #: AF393781; Appl Environ Microbiol. 2002 February; 68(2):807-12)capable of dechlorination of 2,3,5,6-tetrachlorobiphenyl (2,3,5,6-CB) in the absence of sediment was used in this study. Cultures were incubated at 30° C. in the dark. All gases were passed through a column of reduced copper turnings at 350° C. to remove traces of $O_2$. Media (8 ml) were dispersed into culture tubes (16×160 mm) and sealed with Teflon®-lined butyl stoppers (The West Company, Lionville, Pa.) secured by aluminum crimp collars (Bellco Glass, Inc., Vineland, N.J.).

Congener 2,3,5,6-tetrachlorobiphenyl (2,3,5,6-CB) was also solubilized in tetrachloroethene and added to a fresh anaerobic enrichment culture comprising either O-17 or DF-1 and was incubated under strict anaerobic conditions at 30° C. in the dark. Samples (1-1.5 ml) from the both cultures, that being the culture comprising congener 2,3,5,6-tetrachlorobiphenyl (2,3,5,6-CB) alone and in combination with tetrachloroethene, were drawn/removed under anaerobic conditions to determine growth of O-17 or DF-1 bacterium relative to each other It was found that the culture comprising the tetrachloroethene exhibited an increased population growth density during a specific time period relative to the growth density of the culture containing the (2,3,5,6-CB) alone, thereby indicating that the tetrachloroethene stimulated the growth of the bacteria. Further it was found that l While the invention has been described herein in reference to specific aspects, features and illustrative embodiments of the invention, it will be appreciated that the utility of the invention is not thus limited, but rather extends to and encompasses numerous other aspects, features and embodiments. All cited references are herein incorporated in their entirety by reference.

That which is claimed is:

1. A method for stimulating PCB dechlorinating bacteria comprising contacting PCB dechlorinating bacteria with an effective amount of a stimulant, wherein the stimulant comprises at least one polyhalogenated ethene.

2. The method of claim 1, wherein the PCB dechlorinating bacteria comprise strains DF-1 and/or O-17.

3. The method of claim 1, wherein the stimulant comprises tetrachloroethene.

4. The method of claim 1, wherein the stimulant comprises trichloroethene.

5. The method of claim 1, wherein the stimulant comprises dichloroethene.

6. The method of claim 1, wherein the PCB dechlorinating bacteria are contained in soil or sediment.

7. The method of claim 1, wherein the soil or sediment contains PCBs.

8. The method of claims 2, wherein the PCB dechlorinating bacteria are added to solid material before or after contact with the stimulant.

9. The method of claim 2, wherein stimulation of PCB dechlorinating bacteria comprises stimulating the growth and/or PCB dechlorinating activity of said PCB dechlorinating bacteria.

10. A method for dechlorinating polychlorinated biphenyls, comprising contacting soil or sediment containing PCB dechlorinating bacteria with an effective amount of a stimulant, wherein the stimulant comprises at least one polyhalogenated ethene.

11. The method of claim 10, wherein the stimulant comprises tetrachloroethene.

12. The method of claim 10, wherein the stimulant comprises trichloroethene.

13. The method of claim 10, wherein the stimulant comprises dichloroethene.

14. The method of claim 10, wherein the PCB dechlorinating bacteria are added to the soil or sediment.

15. The method of claim 14, wherein the PCB dechlorinating bacteria comprise strains DF-1 and/or O-17.

16. A method for dechlorinating polychlorinated biphenyls, the method comprising:
placing soil or sediment comprising PCBs in a closable container;
introducing into the closable container for contacting with the soil or sediment an effective amount of a stimulant of PCB dechlorinating bacteria, wherein the stimulant comprises at least one polyhalogenated ethene;
incubating the soil or sediment in the closable container for a sufficient time to reduce PCBs in the soil or sediment.

17. The method of claim 16, wherein the stimulant comprises tetrachloroethene.

18. The method of claim 16, wherein the stimulant comprises trichloroethene.

19. The method of claim 16, wherein the stimulant comprises dichloroethene.

20. The method of claim 16, further comprising adding PCB dechlorinating bacteria to the soil or sediment before or after adding said stimulant.

21. A method for dechlorinating polychlorinated biphenyls, the method comprising:
placing soil or sediment comprising PCBs in a closable container, wherein the soil or sediment comprises at least one PCB dechlorinating bacteria;
introducing into the closable container for contact with the soil or sediment an effective amount of a stimulant of PCB dechlorinating bacteria, wherein the stimulant comprises at least one polyhalogenated ethene;
incubating the soil or sediment in the container for a sufficient time to reduce PCBs in the soil or sediment;
purging the closable container with air to remove volatile compounds;

purging the closable container with air or oxygen to stimulate aerobic PCB degrading bacteria; and incubating and aerating the soil or sediment to allow for degradation of the PCBs.

22. The method of claim 21, wherein the stimulant comprises tetrachloroethene.

23. The method of claim 21, wherein the stimulant comprises trichloroethene.

24. The method of claim 21, wherein the stimulant comprises dichloroethene.

25. The method of claim 21, further comprising adding PCB dechlorinating bacteria to the soil or sediment before or after adding said stimulant.

26. A method of culturing PCB dechlorinating bacteria comprising culturing said bacteria in the presence of at least one polyhalogenated ethene.

27. The method of claim 26, wherein the at least one polyhalogenated ethene comprises tetrachloroethene.

28. The method of claim 26, wherein the at least one polyhalogenated ethene comprises trichloroethene.

29. The method of claim 26, wherein the at least one polyhalogenated ethene comprises dichloroethene.

30. The method of claim 26, wherein the at least one polyhalogenated ethane is a member from the group consisting of tetrachloroethene, trichloroethene, trans- and cis-dichloroethene, 1,1-dichloroethene, tetrabromoethene, tribromoethene, trans- and cis-dibromoethene, 1,1-dibromoethene, tetraiodoethene, triiodoethene, trans- and cis-diiodoethene, 1,1-diiodoethene, tetrafluoroethene, trifluoroethene, trans- and cis-difluoroethene, 1,1-difluoroethene, trans- and cis-dibromochloroethene, 1,1-dibromochloroethene, trans- and cis-dichlorobromoethene, 1,1-dichlorobromoethene, trans- and cis-diiodochloroethene, 1,1-diiodochloroethene, trans- and cis-dichloroiodoethene, 1,1-dichloroiodoethene, trans- and cis-difluorochloroethene, 1,1-difluorochloroethene, trans- and cis-dichlorofluoroethene, 1,1-dichlorofluoroethene, trans- and cis-dibromoiodoethene, 1,1-dibromoiodoethene trans- and cis-diiodobromoethene, 1,1-diiodobromoethene, trans- and cis-dibromofluoroethene, 1,1-dibromofluoroethene, trans- and cis-difluorobromoethene, 1,1-difluorobromoethene, trans- and cis-diiodofluoroethene, 1,1-diiodofluoroethene, trans- and cis-difluoroiodoethene and 1,1-difluoroiodoethene.

31. A method for stimulating PCB dechlorinating bacteria comprising contacting PCB dechlorinating bacteria with an effective amount of tetrachloroethene, wherein the PCB dechlorinating bacteria comprises O-17 or DF-1.

32. A method for dechlorinating PCBs, comprising:

placing soil or sediment comprising PCBs in a closable container, wherein the soil or sediment comprises at least one PCB dechlorinating bacteria, and wherein the PCB dechlorinating bacteria comprises O-17 or DF-1;

introducing into the closable container for contact with the soil or sediment an effective amount of a stimulant of PCB dechlorinating bacteria, wherein the stimulant comprises tetrachloroethene;

incubating the soil or sediment in the container for a sufficient time to increase O-17 or DF-1-containing bacteria in the soil or sediment;

purging the closable container with air to remove volatile compounds relating to the breakdown of tetrachloroethene;

incubating the soil or sediment for a sufficient time to reduce PCBs in the soil or sediment;

purging the closable container with air or oxygen to stimulate aerobic PCB degrading bacterial; and incubating and aerating the soil or sediment to allow for degradation of the PCBs.

* * * * *

UNITED STATES PATENT AND TRADEMARK OFFICE
CERTIFICATE OF CORRECTION

PATENT NO.        : 7,462,480 B2
APPLICATION NO.   : 10/502920
DATED             : December 9, 2008
INVENTOR(S)       : Kevin R. Sowers

It is certified that error appears in the above-identified patent and that said Letters Patent is hereby corrected as shown below:

Column 10, line 14: "64(9):3359-67)or" should be -- 64(9):3359-67) or --.

Column 10, line 16: "68(2):807-12)capable" should be -- 68(2):807-12) capable --.

Signed and Sealed this

Twenty-fourth Day of February, 2009

JOHN DOLL
*Acting Director of the United States Patent and Trademark Office*

SEQUENCE LISTING

```
<160> NUMBER OF SEQ ID NOS: 3

<210> SEQ ID NO 1
<211> LENGTH: 1359
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (548)..(548)
<223> OTHER INFORMATION: n = any one of a, c, t, and g.

<400> SEQUENCE: 1
```

-continued

```
gagtttgatc ctggctcagg atgaacgcta gcggcgtgct ttatgcatgc aagtcgaacg      60
gtttttgagt cttcggactt aaaaatagtg gcaaacgggg gagtaacacg taggtaactt     120 accoctaagt ttgggataac tccgggaaac cggggctaat accggatgtg gtgagcgggt     180
aatgcctgtt cactaaagcc ttcgggcgct tggggaaagg cctgcgtccg attagcttgt     240
tggtggggta atggctcacc aaggctatga tcggtagctg gcctgagagg acggtcagcc     300
acactgggac tgagacacgg cccagactcc tacgggaggc agcagcaagg aattttgggc     360
aatgggcgaa agcctgaccc agcaacgccg cgtgggggat gaaggccctc gggttgtaaa     420
ccccttttcc cagggaagaa tgatgacggt acctgggaa taagccccgg ctaactacgt      480
gccagcagcc gcggtaatac gtaggggca agcgttatcc ggatttactg ggcgtaaaga     540
ggacgtangc ggcttttcaa gtcggatgtg aaatttcccg gctcaaccgg gatgagtcat     600
tcgatactgt tgggctagag gatagcaggg ggagacggaa ttcccggtgt agtggtggaa     660
tacgtagata ccgggaggaa caccagaggc gaaggcggtc tccaaggcta tttctgacgc     720
tgaggtccga aagcgtgggt agcaaacaga cttagatact ctggtagtcc acgctgtaaa     780
cgatggacac taggtatagg gagcatcgac cctctttgtg ccgaagctaa cgctttaagt     840
gtcccgcctg gggactacgg ccgcaaggct aaaactcaaa ggaattgacg ggggcccgca     900
caagcagcgg agcgtgtggt ttaattcgat gcaacgcgaa gaaccttacc aaggcttgac     960
atgtcggaag tagtgaaccg aaaggggaac gacccgttaa atcgggagcc gtcacaggtg    1020
ctgcatggct gtcgtcagct cgtgccgtga ggtgtatggt taagtcctgc aacgagcgca    1080
accctcgtcg ctagttgaat tctctagcga ccgcccctg caaaacgggg aggaaggtgg    1140
ggatgacgtc aagtcagcat ggcccttatg ccttgggcta cacacacgct acaatgggtg    1200
gtacagcagg tagcaatagg taacctggag ctaatcccta aaaccatcct cagttcggat    1260
tgtaggctga aactcgcctg catgaagctg gagttgctag taaacgcgta tcagcacggc    1320
gcgttgaata cgttttcggg ccttgtacac accgcccgt                            1359
```

<210> SEQ ID NO 2
<211> LENGTH: 336
<212> TYPE: DNA
<213> ORGANISM: Artificial Sequence
<220> FEATURE:
<223> OTHER INFORMATION: Synthetic Construct

<400> SEQUENCE: 2

```
atggctgtgg tcagctcgtg ccgtgaggtg tttggttaag tcctgcaacg agcgcaaccc      60
tcatcgttag ttgttttctc tagcgagact gccctgcaaa acggggagga aggtggggat    120
gacgtcaagt cagcatggcc cttatgccta gggctacaca cacgctacaa tggtggtac    180 aattggttgc aatggagcaa tccggagcca atccgtaaag ccactctcag ttcggattac    240
aggctgaaac tcgcctgtat gaagtggag ttgctagtaa ccgcaggtca gcatactgcg     300
gtgaatacgt tctcgggcct tgtacacacc gcccgt                               336
```

<210> SEQ ID NO 3
<211> LENGTH: 880
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (66)..(66)
<223> OTHER INFORMATION: n = any one of a, c, t, and g.

-continued

```
<400> SEQUENCE: 3
cagccgccgc ggtaatacgt aggggggcaag cgttatccgg atttactggg cgtaaagagg      60
acgtanggcg gcttttcaag tcggatgtga aatttcccgg ctcaaccggg atgagtcatt     120
cgatactgtt gggctagagg atagcagggg gagacggaat tcccggtgta gtggtggaat     180
acgtagatac cggaggaac accagaggcg aaggcggtct ccaaggctat ttctgacgct      240
gaggtccgaa agcgtgggta gcaaacagac ttagatactc tggtagtcca cgctgtaaac    300
gatggacact aggtataggg agcatcgacc ctctttgtgc cgaagctaac gctttaagtg    360
tcccgcctgg ggactacggc cgcaaggcta aaactcaaag gaattgacgg gggcccgcac    420
aagcagcgga gcgtgtggtt taattcgatg caacgcgaag aaccttacca aggcttgaca    480
tgtcggaagt agtgaaccga aaggggaacg acccggttaa atcgggagcc gtcacaggtg    540
ctgcatggct gtcgtcagct cgtgccgtga ggtgtatggt taagtcctgc aacgagcgca    600
accctcgtcg ctagttgaat tctctagcga gaccgccctg caaaacgggg aggaaggtgg    660
ggatgacgtc aagtcagcat ggcccttatg ccttgggcta cacacacgct acaatgggtg    720
gtacagcagg tagcaatagg gtaacctgga gctaatccct aaaaccatcc tcagttcgga    780
ttgtaggctg aaactcgcct gcatgaagct ggagttgcta gtaaacgcgt atcagcacgg    840
cgcgttgaat acgttttcgg gccttgtaca caccgcccgt                          880
```